Nov. 26, 1963 D. H. MOREY, JR Plant Pat. 2,322
ROSE PLANT
Filed Oct. 24, 1962
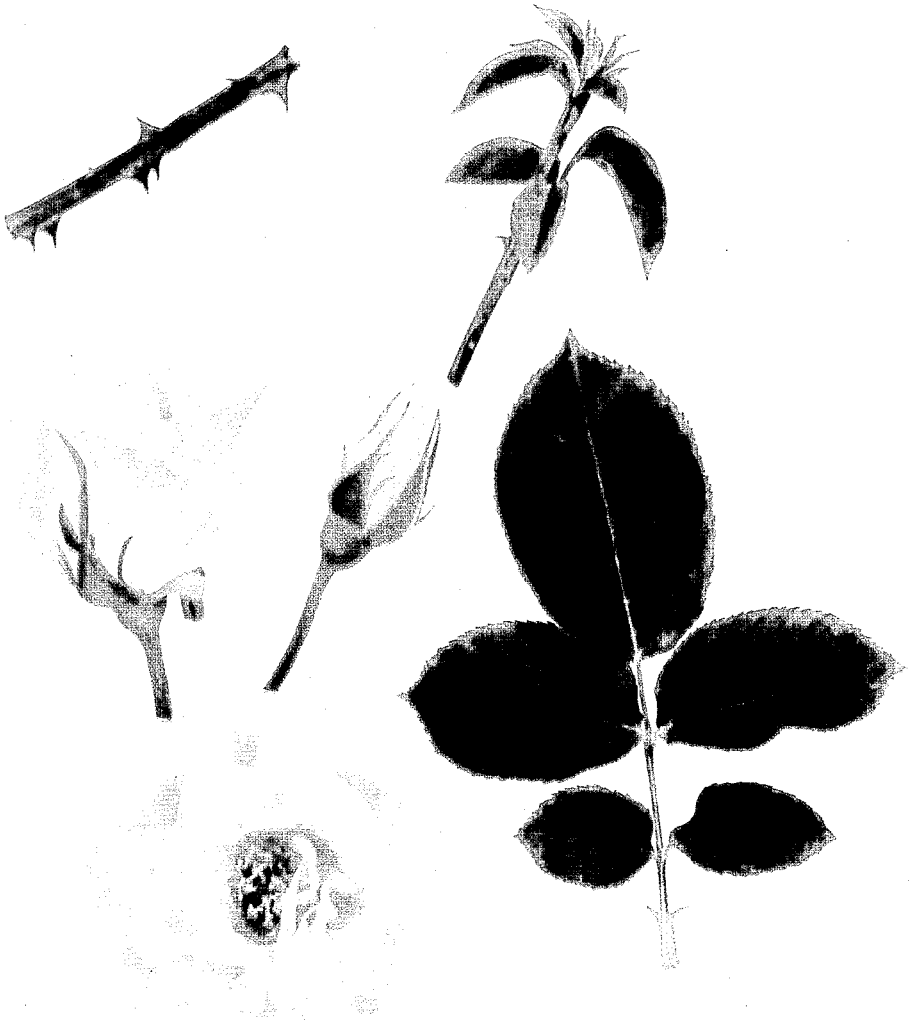
Inventor
Dennison H. Morey, Jr.
By: Robb + Robb
Attorneys.

United States Patent Office

Plant Pat. 2,322

Patented Nov. 26, 1963

2,322

ROSE PLANT

Dennison H. Morey, Jr., Pleasanton, Calif., assignor to Jackson & Perkins Company, Newark, N.Y., a corporation of New York Filed Oct. 24, 1962, Ser. No. 232,916

1 Claim. (Cl. Plt.—2)

The present invention relates to a new and distinct variety of rose plant of the climber class, which was originated by me by crossing an unnamed and unpatented seedling derived from a cross of "Captain Thomas" (Plant Patent No. 393) × "Joanna Hill" (unpatented) with the variety "Mme. Kriloff" (unpatented).

The primary objective of this breeding was to produce a new variety of climbing rose which bears flowers of the color and size of those of the parent variety "Mme. Kriloff." This objective was fully achieved, along with other desirable improvements, as evidenced by the following unique combination of characteristics which are outstanding in the new variety and which distinguish it from its parents, as well as from all other varieties of which I am aware:

(1) A habit of producing individual shoots ranging from 6 to 8 feet tall;

(2) Large, glossy foliage;

(3) Abundant spring blooms, with continuous summer remontance;

(4) Large flower size;

(5) A distinctive and interesting flower bud color corresponding to Scarlet Red, lightly overcast with Rose Doree;

(6) A distinctive and attractive general color tonality of the open flowers corresponding to Grenadine Pink, lightly overcast with Strawberry Pink; and (7) A strong, fruity flower fragrance.

Asexual reproduction of my new variety by budding, as performed at Pleasanton, California, and also at Newark, New York, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed seedling of "Captain Thomas" × "Joanna Hill."

*Pollen parent.*—"Mme. Kriloff."

Classification:

*Botanic.*—Climber.

*Commercial.*—Climber.

*Flower*

(Observations made from specimens grown outdoors at Newark, New York, near mid-morning during the latter part of the month of June.)

Blooming Habit: Recurrent — continuous; abundant blooms in spring with continuous summer remontance.

Bud:

*Size.*—Large.

*Form.*—Pointed; is not affected by wet or hot weather.

*Color.*—When sepals first divide — Jasper Red, Plate 13. When petals begin to unfurl—Deep Chrome, Plate 3, with upper half of petals overcast with Grenadine Red, Plate 2. When half-blown: inside of petals—Scarlet Red, Plate 1, lightly overcast with Rose Doree, Plate 1; reverse of petals—Light Orange-Yellow, Plate 3, with upper half of petals overcast with Geranium Pink, Plate 1.

*Sepals.*—Slightly branched; curl back when petals begin to unfurl. Color: inside—Pale Olivine, Plate 32; outside—Chromium Green, Plate 32, lightly overcast with Light Brownish Olive, Plate 30.

*Calyx.* — Color — Shamrock Green, Plate 32. Shape—apple. Size—small. Aspect — smooth. Odor when rubbed—none.

*Peduncle.*—Length — medium. Aspect — prickly. Strength—erect; slender. Color—Parrot Green, Plate 6, slightly overcast with Russet, Plate 15.

Bloom:

*Size.*—Large. Average size when fully expanded—6 inches.

*Borne.*—Several together and in rounded clusters.

*Stems.*—Medium length; strong.

*Form (when first open).*—High centered. Permanence—retains its form to the end, but outer petals curl back.

*Petalage.*—Double (full but open center). Number of petals under normal conditions—40.

*Color.*—Center of flower—Rose Doree, Plate 1, lightly overcast with Peach Red, Plate 1. Outer petals —Flesh Color, Plate 14, very lightly overcast with Strawberry Pink, Plate 1. Base of petals (aiglet) —Lemon Chrome, Plate 4. Inside of petals—Grenadine Pink, Plate 2, lightly overcast with Strawberry Pink, Plate 1, and with lower half of petals very lightly overcast with Empire Yellow, Plate 4. Reverse of petals—Pale Yellow-Orange, Plate 3, with outer edge of petals very lightly overcast with Geranium Pink, Plate 2. General tonality from a distance—Grenadine Pink, Plate 2, lightly overcast with Strawberry Pink, Plate 1.

*Discoloration.*—General tonality at end of first day—Rose Doree, Plate 1, lightly overcast with Peach Red, Plate 1. Second day—Grenadine Pink, Plate 2, lightly overcast with Strawberry pink, Plate 1. Third day—Grenadine Pink, Plate 2, lightly overcast with Strawberry Pink, Plate 1.

Petals:

*Texture.*—Leathery; is not affected by wet or hot weather.

*Appearance.*—Inside—satiny. Outside—shiny.

*Form.*—Oval.

*Arrangement.*—Imbricated (regularly arranged shingle-like).

*Petaloids in center.*—Few; large.

*Persistence.*—Drop off cleanly.

*Fragrance.*—Strong. Nature—fruity (russet apple).

*Lasting quality.* — On the plant — long. As cut flower—long.

*Genital Organs*

Stamens, anthers: Medium size; many; regularly arranged around styles. Color—Light Cadmium, Plate 4.

Stamens, filaments (threads): Long. Color — Coral Red, Plate 13.

Pollen: Color—Maize Yellow, Plate 4.

Styles: Columnar; uneven length; medium length; thin.

Stigmas: Color—Cream Buff, Plate 30.

Ovaries: All enclosed in calyx.

Hips: None.

Seeds: None.

*Plant*

Form: Climber.

Growth: Very vigorous; upright; shoots attain height ranging from 6 to 8 feet.

Foliage: Compound of 5–7 leaflets.

*Size.*—Large.

*Quantity.*—Abundant.

*Color.* — New foliage: upper side — Yellowish Oil Green, Plate 5; under side—Van Dyke Red, Plate 13. Old foliage: upper side — Varley's Green, Plate 18; under side — Light Cress Green, Plate 31.

*Shape.*—Oval.

*Texture.*—Upper side—glossy. Under side—smooth.

*Ribs and veins.*—Ordinary.

*Edge.*—Both double and single; small.

*Leaf stem.*—Color—Fawn Color, Plate 40. Under side—prickly.

*Stipules.*—Medium length; bearded.

Wood:

*New wood.*—Color—Chromium Green, Plate 32, lightly overcast with Brick Red, Plate 13. Bark—smooth.

*Old wood.*—Color—Varley's Green, Plate 18. Bark—smooth.

Thorns:

*Thorns.*—Quantity: on main stalks from base—ordinary; on laterals from stalk—ordinary. Form—flat base; medium length; hooked downward. Color (when young)—Eugenia Red, Plate 13. Position—irregular.

*Prickles.*—Quantity: on main stalks—none; on laterals—none.

*Short needles.* — Quantity: on main stalks — none; on laterals—none.

I claim:

A new and distinct variety of rose plant of the climber class, substantially as herein shown and described, characterized particularly as to novelty by the unique combination of a habit of producing individual shoots ranging from 6 to 8 feet tall, large, glossy foliage, the production of abundant spring blooms, with continuous summer remontance, large flower size, a distinctive and interesting flower bud color corresponding to Scarlet Red, lightly overcast with Rose Doree, a distinctive and attractive general color tonality of the open flowers corresponding to Grenadine Pink, lightly overcast with Strawberry Pink, and a strong fruity flower fragrance.

No references cited.